US011039900B2

(12) United States Patent
Hallack et al.

(10) Patent No.: US 11,039,900 B2
(45) Date of Patent: Jun. 22, 2021

(54) CONTROL FOR ADAPTIVE LIGHTING ARRAY

(71) Applicants: Gentex Corporation, Zeeland, MI (US); Mayo Foundation for Medical Education and Research, Rochester, MN (US)

(72) Inventors: Jason D. Hallack, Holland, MI (US); Bradley R. Hamlin, Allendale, MI (US); David M. Falb, Grand Rapids, MI (US); Jeremy A. Schut, Grand Rapids, MI (US); Danny L. Minikey, Jr., Fenwick, MI (US); Mark A. VanVuuren, Dorr, MI (US); David J. Wright, Grand Rapids, MI (US)

(73) Assignees: GENTEX CORPORATION, Zeeland, MI (US); MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 16/732,577

(22) Filed: Jan. 2, 2020

(65) Prior Publication Data

US 2020/0214787 A1 Jul. 9, 2020

Related U.S. Application Data

(60) Provisional application No. 62/788,400, filed on Jan. 4, 2019.

(51) Int. Cl.
*A61B 90/35* (2016.01)
*H05B 47/125* (2020.01)
(Continued)

(52) U.S. Cl.
CPC .......... *A61B 90/35* (2016.02); *A61B 90/361* (2016.02); *H04N 5/2354* (2013.01);
(Continued)

(58) Field of Classification Search
CPC . A61B 90/35; A61B 90/361; A61B 2090/363; H04N 5/23218; H04N 5/2354; H05B 47/125
See application file for complete search history.

(56) References Cited

U.S. PATENT DOCUMENTS 6,079,862 A 6/2000 Kawashima et al.
7,706,683 B2 4/2010 Rossner et al.
(Continued)

FOREIGN PATENT DOCUMENTS

CN 107799171 A 3/2018
KR 20160007700 A 1/2016
KR 20180057447 A 5/2018

*Primary Examiner* — Richard A Hansell, Jr.
(74) *Attorney, Agent, or Firm* — Price Heneveld LLP; Bradley D. Johnson

(57) ABSTRACT

An illumination system for a room comprises a light assembly comprising at least one illumination source configured to selectively direct at least one light emission in an operating region of the room. The system further comprises an imager configured to capture image data in a field of view in the room. A controller is in communication with the light assembly and the imager. The controller is configured to detect a position of the marker in the image data and control the light assembly to direct the at least one light emission within the operating region based on the position of the marker.

16 Claims, 8 Drawing Sheets

(51) Int. Cl.
     *H04N 5/235*        (2006.01)
     *H04N 5/232*        (2006.01)
     *A61B 90/00*        (2016.01)

(52) U.S. Cl.
     CPC ....... *H04N 5/23218* (2018.08); *H05B 47/125* (2020.01); *A61B 2090/363* (2016.02)

(56) References Cited

U.S. PATENT DOCUMENTS

| | | |
|---|---|---|
| 8,736,548 B2 | 5/2014 | Pryor |
| 8,817,085 B2 * | 8/2014 | Hiltl ........................ A61B 90/30 |
| | | 348/61 |
| 2008/0177569 A1 | 7/2008 | Chen et al. |
| 2008/0256494 A1 * | 10/2008 | Greenfield ......... G06K 9/00355 |
| | | 715/863 |
| 2011/0037840 A1 * | 2/2011 | Hiltl ........................ A61B 90/35 |
| | | 348/61 |
| 2017/0296290 A1 * | 10/2017 | Nieminen ............... A61B 90/36 |
| 2017/0367785 A1 * | 12/2017 | Munari ................ H05B 47/105 |
| 2019/0060026 A1 * | 2/2019 | Geerlings ............... A61B 90/39 |
| 2019/0282307 A1 * | 9/2019 | Azizian ................. A61B 34/20 |

* cited by examiner

CONTROL FOR ADAPTIVE LIGHTING ARRAY

CROSS-REFERENCE TO RELATED APPLICATIONS

This application claims priority under 35 U.S.C. § 119(e) and the benefit of U.S. Provisional Application No. 62/788,400 entitled CONTROL FOR ADAPTIVE LIGHTING ARRAY, filed on Jan. 4, 2019, by Jason D. Hallack et al., the entire disclosure of which is incorporated herein by reference.

FIELD OF THE DISCLOSURE

The present disclosure generally relates to illumination systems, and more particularly, to a surgical theater and surgical suite illumination systems.

BACKGROUND OF THE DISCLOSURE

Artificial lighting provided in surgical theaters and surgical suites may present a number of issues with regard to positioning, shadows, luminosity, and glare. Often, medical professionals are not stationary and the lighting needs to be dynamic due to the shifting of personnel and instruments throughout the surgical procedure. Further, differences in the physical dimensions of personnel may make positioning light sources challenging. Accordingly, new illumination systems for surgical suites may be advantageous.

SUMMARY OF THE PRESENT DISCLOSURE

According to one aspect of this disclosure, an illumination system for a room is disclosed. The system comprises a light assembly comprising at least one illumination source configured to selectively direct at least one light emission in an operating region of the room. The system further comprises an imager configured to capture image data in a field of view in the room. A controller is in communication with the light assembly and the imager. The controller is configured to detect a position of the marker in the image data and control the light assembly to direct the at least one light emission within the operating region based on the position of the marker.

According to another aspect of this disclosure, a method for controlling a light assembly comprising at least one illumination source configured to selectively direct a plurality of light emissions in an operating region of a room. The method comprising capturing image data in a field of view in the room, detecting a position of the marker in the image data; and directing a first light emission within the operating region based on the position of the marker. The method further comprises detecting the marker in the image data entering the operating region of the field of view from outside an operating perimeter of the operating region. In response to detecting the marker entering the operating region, the method further comprises controlling the light assembly to direct a second light emission within the operating region based on the position of the marker.

According to yet another aspect of this disclosure, an illumination system for a room is disclosed. The system comprises a light assembly comprising at least one illumination source configured to selectively direct at least one light emission in an operating region of the room. An imager is configured to capture image data in a field of view in the room. A controller is in communication with the light assembly and the imager. The controller is configured to control the light assembly to direct the at least one emission illuminating a lighting region of the operating region and detect a position of the marker in the image data. The controller is further configured to selectively control a target location of the at least one light emission in response to identifying the marker proximate to the lighting region for a predetermined period of time. In response to identifying a change in the position of the marker at a rate of motion within a predetermined velocity range in the field of view, the controller is configured to track the motion of the marker within the operating region and adjust the target location of the at least one light emission to change commensurate to the motion of the marker within the operating region. The controller is further configured to control the light assembly to direct the at least one light emission to impinge upon the target location in response to the change in the target location.

These and other aspects, objects, and features of the present disclosure will be understood and appreciated by those skilled in the art upon studying the following specification, claims, and appended drawings. It will also be understood that features of each example disclosed herein may be used in conjunction with, or as a replacement for, features of the other examples.

BRIEF DESCRIPTION OF THE DRAWINGS

The following is a description of the figures in the accompanying drawings. The figures are not necessarily to scale, and certain features and certain views of the figures may be shown exaggerated in scale or in schematic in the interest of clarity and conciseness.

In the drawings.

DETAILED DESCRIPTION

Figure 1:
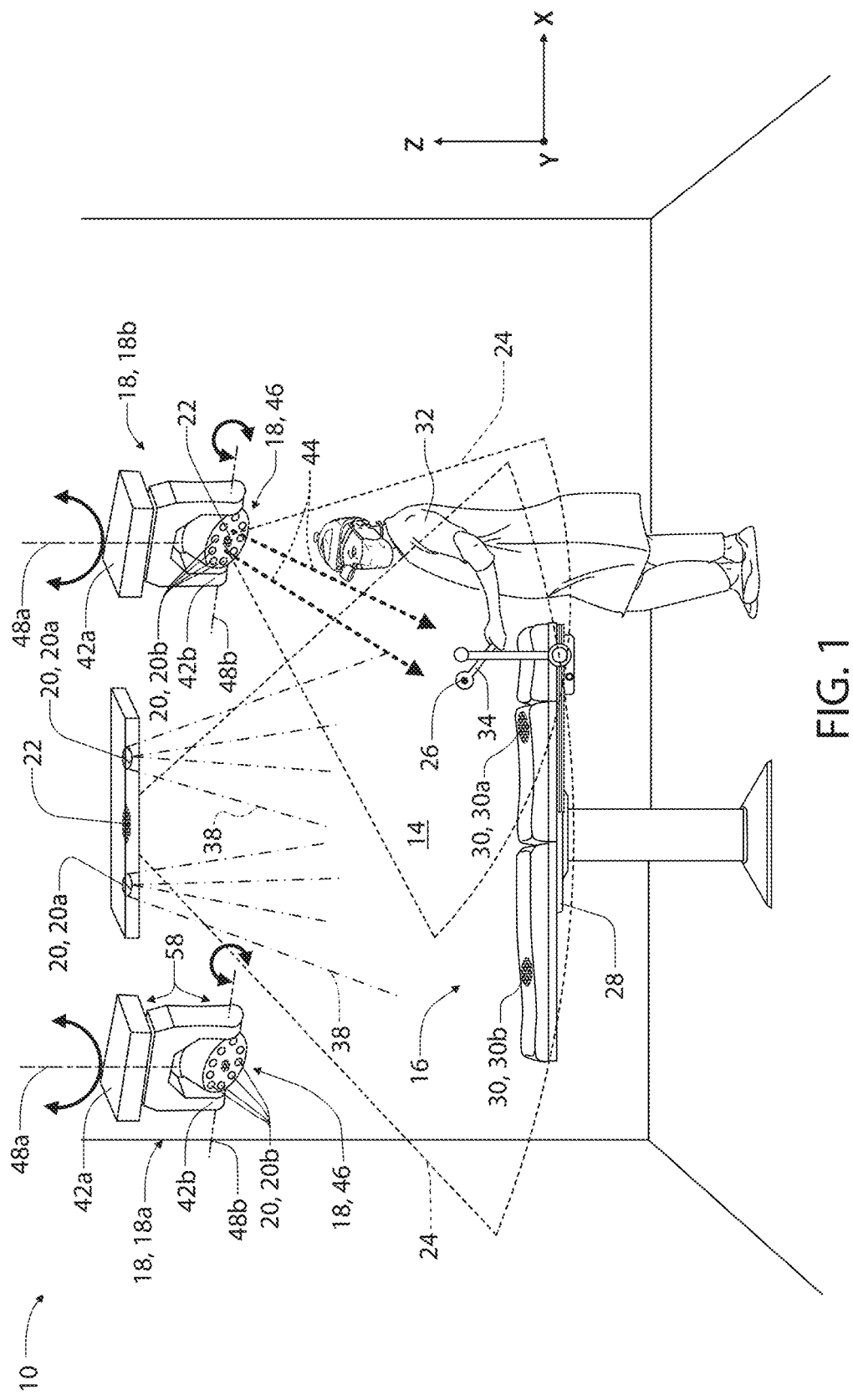
FIG. 1 is a schematic view of a surgical suite comprising an illumination system.

Additional features and advantages of the invention will be set forth in the detailed description which follows and will be apparent to those skilled in the art from the description or recognized by practicing the invention as described in the following description together with the claims and appended drawings.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Referring generally to FIGS. 1-4, the disclosure provides for an illumination system 10. The illumination system 10 may comprise a controller 12 and various accessories that may be utilized in a medical suite 14 to selectively illuminate a location or operating region 16. The illumination system 10 may comprise one or more light assemblies 18, which may include one or more light sources 20. Additionally, the system 10 may comprise at least one imager 22 operable to capture image data in a field of view 24 comprising the operating region 16. In an exemplary embodiment, the controller 12 of the system 10 may be configured to scan the operating region 16 to identify a location of a marker 26. Based on the location of the marker 26, the controller 12 may control a lighting emission from the one or more light sources 20 to illuminate the location corresponding to the position of the marker 26 identified in the image data. In this way, the system 10 may provide for a computer-assisted control of a direction of lighting emissions directed from the one or more light sources to conveniently illuminate various locations within the operating region 16.

In some examples, the system 10 may be configured to illuminate a plurality of positions or target regions 30, which may be located within the operating region 16. The target regions 30 may comprise at least a first target region 30a and a second target region 30b. In such cases, the system 10 may be configured to track the motion of the marker 26 to independently adjust the position of each of the target regions 30. Such tracking may be at least partially determined by the controller 12 of the system 10 by detecting motion and/or rate of motion of the marker 26 in the field of view 24. Additionally, the controller 12 may be configured to identify one or more gestures and/or tracking cues that may be controlled by a user 32 by manipulating or adjusting a position of a control instrument 34 comprising the marker 26. Various examples of such operations are discussed in reference to FIGS. 5-8. Accordingly, the disclosure may provide for a variety of operating methods that may provide for the system to be controlled intuitively and efficiently without unnecessary distractions.

Referring now to FIG. 1, reference numeral 10 generally designates an illumination system 10. The illumination system 10 is depicted in a medical suite 14 and includes one or more light assemblies 18. The light assemblies 18 may include one or more light sources 20. The illumination system 10 may include one or more imagers 22 depicted to aid in the use of the illumination system 10. The imagers 22 may be positioned within or coupled to the light assemblies 18 (e.g., in handles or bodies), a table 28, and/or around the medical suite 14. The imager 22 may be a charge-coupled device (CCD) imager, a complementary metal-oxide-semiconductor (CMOS) imager, other types of imagers, and/or combinations thereof. According to various examples, the imager 22 may include one or more lenses to collimate and/or focus the light reflected by the patient, the table 28, or other features of the medical suite 14.

The table 28 may at least partially define the operating region 16. For purposes of this disclosure, the operating region 16 may be an operating field which is an isolated area where surgery is performed and may include all furniture and equipment covered with sterile drapes and all personnel being properly attired. Although described in connection with the medical suite 14, it will be understood that the illumination system 10 of the present disclosure may be utilized in a variety of environments. For example, the illumination system 10 may be utilized in automobile repair areas, doctor's offices, dentistry, photography studios, manufacturing settings, as well as other areas where dynamic lighting solutions may be advantageous.

The table 28 is configured to support a patient during a surgical procedure. According to various examples, the table 28 may have a square, rectangular and/or oval configuration. The table 28 may be composed of a metal (e.g., stainless steel), a polymer and/or combinations thereof. According to various examples, a sterile covering (e.g., a cloth or paper) may be positioned across a surface of the table 28. The table 28 may be configured to tilt, rotate and/or be raised or lowered. In examples where the table 28 is configured to tilt, the table 28 may tilt an angle from about 1° to about 10° about a long or a short axis of the table 28. The tilting of the table 28 may be performed in conjunction with illumination provided from the illumination system 10 and/or the light assemblies 18. For example, the table 28 may be configured to tilt toward and/or away from the light assemblies 18 to increase illumination, decrease illumination and/or to eliminate glare reflecting off of the patient and/or table 28. Further, tilting of the table 28 may be advantageous in allowing users (e.g., medical personnel) positioned around the table 28 to more easily access the patient and/or surgical field. In addition to tilting, it will be understood that the table 28 may be configured to raise or lower, rotate and/or slide about an X-Y plane.

The light assemblies 18 may take a variety of configurations. The light assemblies may include one or more light sources 20. In a first example, the light assemblies 18 may be modular and interconnected and supported on a track system. For example, the light assemblies 18 may have a circular, oval, oblong, triangular, square, rectangular, pentagonal or higher-order polygon shape. It will be understood that different light assemblies 18 may be provided in different forms and that the illumination system 10 may include a variety of light assemblies 18.

The operating region 16 may be illuminated by a detection emission 38, shown projected in a field of view 24 of the imager 22. The detection emission 38 may be emitted from one or more of the light sources 20 in a substantially non-visible wavelength of light. In an exemplary embodiment, the detection emission 38 may be emitted from a detection emitter 20a as infrared light (e.g., near-infrared, infrared, and/or far-infrared). In this configuration, the operating region 16 may be illuminated by the detection emission 38 illuminating various objects that enter the field of view 24 of the imager 22. Accordingly, the marker 26 may be illuminated by the detection emission 38 from the emitter 20a such that the reflected light from the detection emission 38 is captured in the image data of the imager 22. To improve the intensity of the detection emission 38 reflected back to the imager 22, in some embodiments, the marker 26 may comprise a reflective surface finish configured to reflect the detection emission 38.

In various examples, the light assemblies 18 may be positioned or suspended from one or more positioning assemblies 40, which may adjust a projection direction of the light sources 20 by controlling one or more actuators 42. Accordingly, the positioning assemblies may be configured to rotate and/or translate independently or in any combination. As shown, the system 10 may comprise a first positioning mechanism 40a and a second positioning mechanism 40b. In general, the positioning assemblies 40 as discussed herein may be configured to control a direction of one or more lighting emissions 44 emitted from the one or more visible light sources 20b. As demonstrated and further discussed further herein, each of the light sources 20 as well as the positioning assemblies 40 may be in communication with the controller 12, which may be configured to control a direction of the one or more lighting emissions 44 to illuminate the location of the marker 26 with visible light. In this way, the system 10 may be operable to control one or more of the visible light sources 20b to illuminate the marker 26 or various portions of the operating region 16.

In various embodiments, the one or more positioning assemblies 40 may comprise one or more gimbaled arms, which may be maneuvered or adjusted in response to a movement (e.g., rotational actuation) of one or more actuators 42a and 42b. In this configuration, the controller 12 may be configured to control each of the actuators 42a and 42b to manipulate the orientation of a lighting module 46 comprising one or more of the visible light sources 20b and/or the detection emitters 20a. In this way, the positioning assembly 40 may control the rotation of the lighting module 46 about a first axis 48a and a second axis 48b. Such manipulation of the lighting module 46 may enable the controller 12 to direct the light sources 20b to selectively illuminate the operating region 16 or various portions of the medical suite 14 in response to the detected location of the marker 26.

The positioning assemblies 40 and actuators 42a and 42b, as discussed herein, may correspond to one or more electrical motors (e.g., servo motors, stepper motors, etc.). Accordingly, each of the positioning assemblies 40 (e.g., the actuators 42) may be configured to rotate the lighting module 360 degrees or within the boundary constraints of lighting modules 46 or other support structures that may support the lighting modules 46. The controller 12 may control the motors or actuators 42 of the lighting modules 46 to direct the lighting emissions 44 of the visible light sources 20b to target a desired location in the medical suite 14. In order to accurately direct the lighting module 46 to target the desired location, the controller 12 may be calibrated to control the position of the lighting module 46 to target locations in a grid or work envelope of the medical suite 14. The calibration of such a system may require maintenance in the form of calibration updates or compensation due to variations in the operation of the positioning assemblies 40 and actuators 42 that may occur over time.

Still referring to FIG. 1, in operation, the marker 26 may be illuminated by the detection emission 38 in the field of view 24 such that the imager 22 may capture the reflection of the marker 26 in image data. In some embodiments, the imager 22 may comprise one or more filters that may limit the transmission of wavelengths of light that are not included in the detection emission 38 such that the reflection of the detection emission 38 may be readily identifiable. Once the image data comprising the reflection of the marker 26 is captured, the image data may be communicated to the controller 12 such that the location of the marker 26 may be identified in the field of view 24. Based on the location of the marker 26, the controller 12 may control a lighting emission 44 from the one or more light sources 20 to illuminate the location corresponding to the position of the marker 26. The light sources 20 configured to emit the lighting emission 44 may be referred to as visible light sources 20b. In this way, the system 10 may provide for a computer-assisted control of a direction of lighting emissions directed from the one or more light sources to conveniently illuminate various locations within the operating region 16.

In some embodiments, the illumination system 10 may comprise a plurality of imagers 22 which capture image data from the medical suite 14 and/or from the operating region 16. The imagers 22 may be configured to relay image data to the controller 12 of the illumination system 10. The controller 12 may include a memory and a processor. The memory may store computer-executable commands (e.g., routines) which are controlled by the processor. According to various examples, the memory may include a light control routine and/or an image analyzing routine. The image analyzing routine is configured to process data from the imager 22. For example, the image analyzing routine may be configured to identify shadows and luminosity of the operating region 16, the light from the guidance system, location of points of interest (e.g., users around the table 28) and/or gestures from the users.

According to various examples, the image analyzing routine may also be configured to identify the location of the marker 26 in the image data. The marker 26 may include one or more symbols, computer-readable codes and/or patterns that designate a point of interest in the image data. For example, the marker 26 can be positioned around the operating region 16 such that the image analyzing routine may identify the location of the marker 26 in the operating region 16. The marker 26 may be disposed on one or more instruments, points of interest in the medical suite 14, and/or the patient.

Once the image analyzing routine has processed the data from the imager 22, the light control routine may control how the positioning assemblies 40 are operated. For example, the light control routine may be configured to move, steer, activate or otherwise influence the light assemblies 18 to emit light at the location of the marker 26. Such a location may correspond to an area of interest where the user is looking or working (e.g., as measured from the guidance system). In this way, the light control routine may steer or otherwise move the one or more visible light sources 20b to emit the lighting emission 44 to illuminate various areas where the user is looking and/or where hands and instruments may be positioned.

As discussed herein, the illumination system 10 and/or the disclosure provided above are configured to operate in conjunction with a number of other features present in the medical suite 14. For example, the illumination system 10 may be configured to track the location and use of the marker 26, which may be coupled to one or more instruments. The instruments may be coded based on type (e.g., consumable tool vs. non-consumable) and/or by the operator using or placing them. The instruments may be tracked as they enter and exit the operating region 16 in response to a detection of the marker 26 in image data captured by the imager 22. In yet other examples, one or more of the instruments may include a radio frequency identification tracking device.

Figure 2:
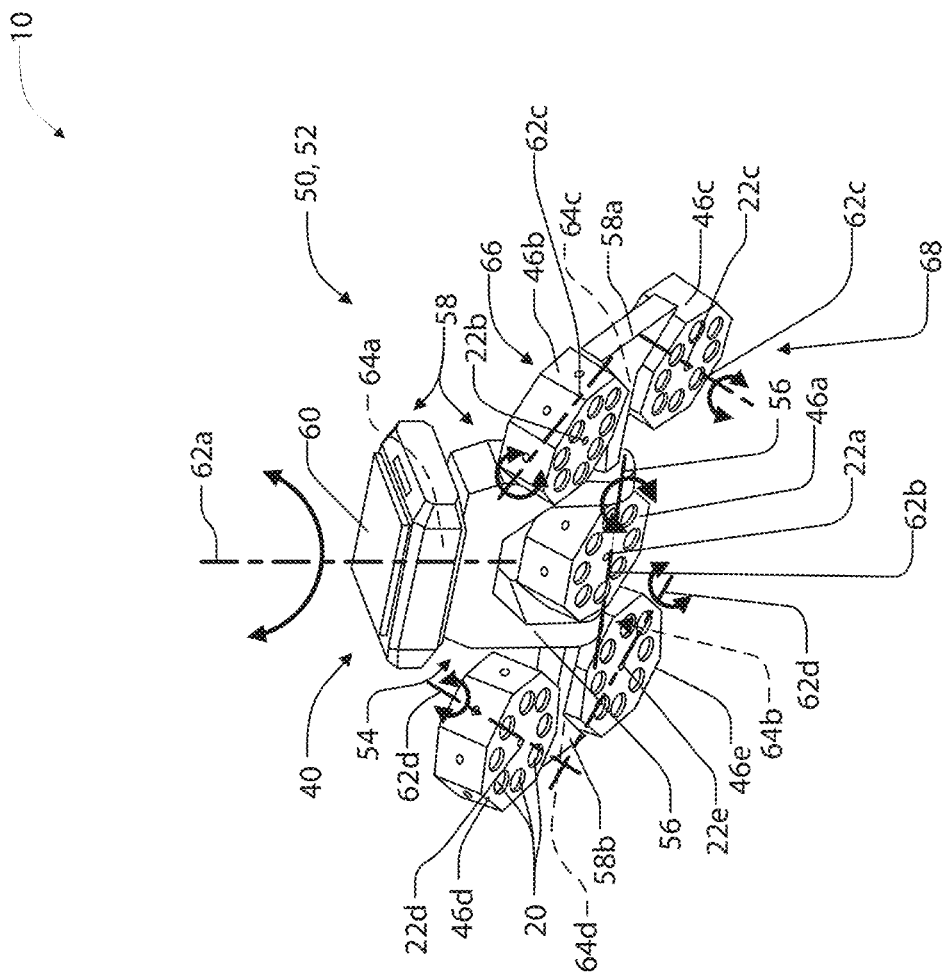
FIG. 2 is a schematic view lighting module of an illumination system.

Referring now to FIG. 2, a schematic view of the illumination system 10 is shown comprising an exemplary implementation of the positioning assembly 40 referred to as an articulating head assembly 50. Each of the articulating head assemblies 50 or articulating assemblies 50 may comprise a lighting module array 52 of the lighting modules 46. Each of the articulating head assemblies 50 may serve as an exemplary embodiment of the one or more positioning assemblies 40 in accordance with the disclosure. In the exemplary embodiment shown, the articulating head assembly 50 comprises five of the lighting modules 46. The lighting modules 46 may be suspended from a central control arm 54 comprising a plurality of support arms 56. Extending from each of the support arms 56, a lateral support beam 58 or wing may extend laterally outward from each of the arms 56 in opposing directions. In this configuration, the lighting modules 46 are supported by the central control arm 54 in a distributed arrangement.

The central control arm 54 may be suspended from a support housing 60 along a first axis 62a (e.g., Y-axis). The support housing 60 may comprise the controller 12 and a first actuator 64a configured to rotate the central control arm 54 about the first axis. A first lighting module 46a may be suspended along a second axis 62b (e.g., X-axis) extending between the support arms 56. A second actuator 64b may be in connection with the support arms 56 and the first lighting module 46a. The second actuator 64b may be configured to rotate the first lighting module 46a about the second axis 62b. In this configuration, the controller 12 may control the emission direction of the first lighting module 46a to rotate approximately 360 degrees about the first axis 62a and the second axis 62b.

Each of the lateral support beams 58 may support a pair of the lighting modules 46. That is, a first support beam 58a may support a second lighting module 46b on a first side 66 and a third lighting module 46c on a second side 68. The first side 66 and the second side 68 of the first support beam 58a may extend in opposing directions from the first support beam 58 along a third axis 62c. A second support beam 58b may support a fourth lighting module 46d on the first side 66 and a fifth lighting module 46e on the second side 68. The first side 66 and the second side 68 of the second support beam 58b may extend in opposing directions from the first support beam 58 along a fourth axis 62d. The third axis 62c and the fourth axis 62d may extend perpendicular to the second axis 62b.

Each of the first support beam 58a and the second support beam 58b may connect to each of the support arms 56 and rotate about the second axis 62b with the first lighting module 46a. Additionally, each of the lateral support beams may comprise at least one actuator configured to rotate the lighting modules 46b, 46c, 46d, and 46e about the third axis 62c and the fourth axis 62d. For example, the first support beam 58a may comprise a third actuator 64c in connection with the second lighting module 46b and the third lighting module 46c along the third axis 62c. The second support beam 58b may comprise a fourth actuator 64d in connection with the fourth lighting module 46d and the fifth lighting module 46e along the fourth axis 62d. In this configuration, the controller 12 may control the second actuator 64b to rotate each of the lighting modules 46b, 46c, 46d, and 46e about the second axis 62b. Additionally, the controller 12 may control the third actuator 64c to rotate the second and third lighting modules 46b and 46c about the third axis 62c.

Finally, the controller 12 may control the fourth actuator 64d to rotate the fourth and fifth lighting modules 46d and 46e about the fourth axis 62d.

As previously discussed, each of the light modules 46 may comprise an imager 22. In some embodiments, the articulating head assembly 50 may comprise a single imager 22 or an imager array. For example, the imager array may be formed as follows: the first lighting module 46a may comprise a first imager 22a, the second lighting module 46b may comprise a second imager 22b, the third lighting module 46c may comprise a third imager 22c, the fourth lighting module 46d may comprise a fourth imager 22d, and/or the fifth lighting module 46e may comprise a fifth imager 22e. Each of the imagers 22 may be configured to capture the image data in corresponding fields of view 24a, 24b, 24c, 24d, and 24e (not shown for clarity). The controller 12 may process the image data from each of the imagers 22 to identify a region of interest. Accordingly, the controller 12 may scan the image data from each of the imagers 22 and adjust the orientation of each of the lighting modules 46 to dynamically control the light in the surgical suite 14.

Though the imagers 22 are discussed as being incorporated on each of the lighting modules 46, the system 10 may be configured to capture image data from any location in the surgical suite 14. As further discussed in reference to FIG. 3, a plurality of the articulating head assemblies 50 may be controlled by a central controller in communication with each of the controllers 12. In such embodiments, the central controller may be configured to process the image data from the one or more imagers 22 and communicate control signals for each of the plurality of lighting modules 46 and the actuators 64 of the articulating head assemblies 50. Accordingly, the system 10 may be implemented in a variety of beneficial embodiments without departing from the spirit of the disclosure.

Figure 3:
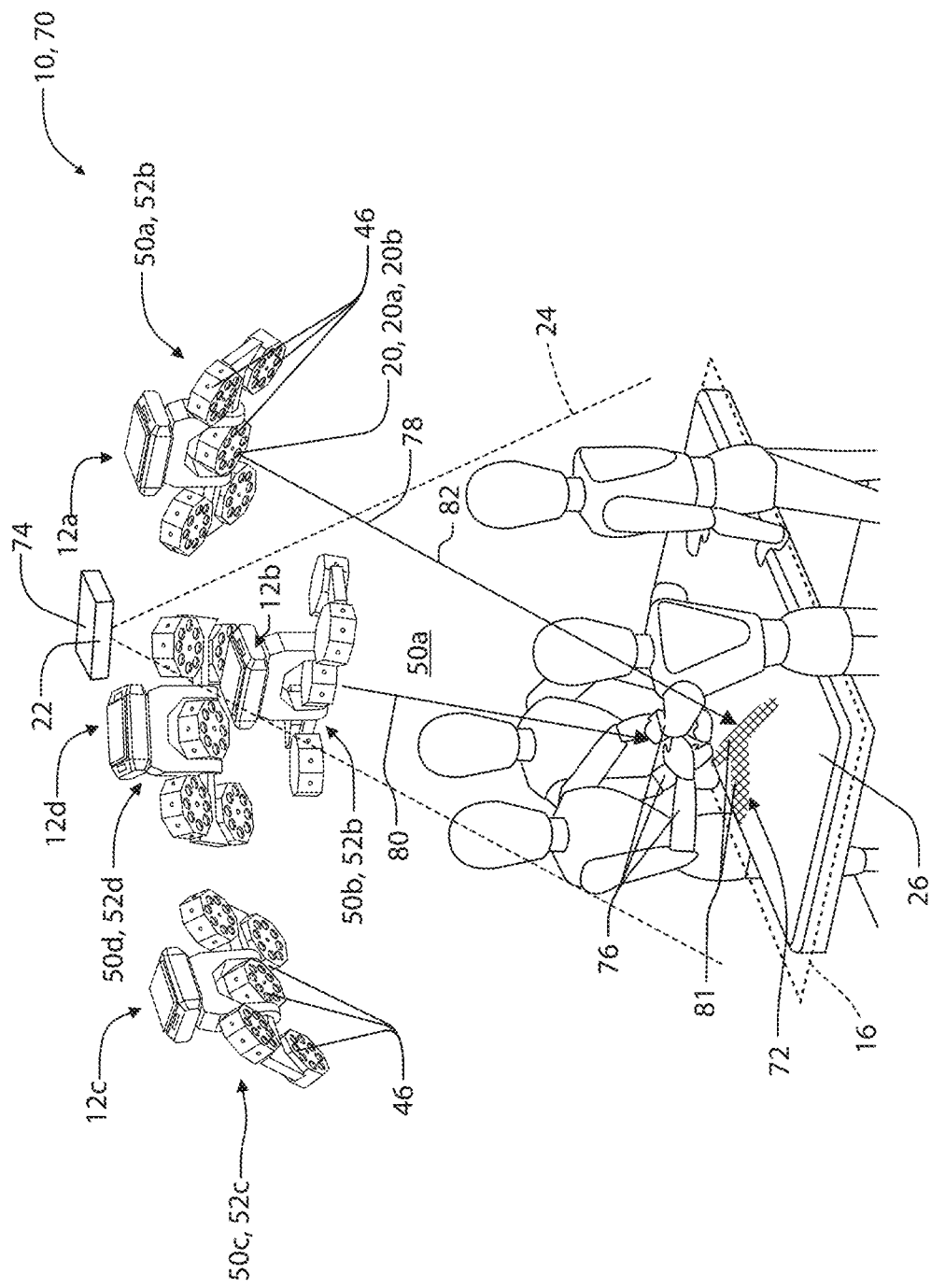
FIG. 3 is a schematic view of an illumination system comprising an articulating head assembly including an array of lighting modules.

FIG. 3 is a schematic view of the illumination system 10 comprising a head assembly array 70 formed of the articulating head assemblies 50. Each of the articulating head assemblies 50 may comprise the lighting module array 52. As demonstrated, the head assembly array 70 comprises a first head assembly 50a, a second head assembly 50b, a third assembly 50c, and a fourth head assembly 50d. Each of the head assemblies 50 comprises a corresponding lighting module array 52. For example, the first head assembly 50a comprises the first lighting module array 52a, the second head assembly 50b comprises the second lighting module array 52b, the third head assembly 50c comprises the third lighting module array 52c, and the fourth head assembly 50d comprises the fourth lighting module array 52d.

Each of the head assemblies 50 of the head assembly array 70 may comprise a controller 12 (e.g., a first controller 12a, a second controller 12b, a third controller 12c, and a fourth controller 12d). The controllers 12 may be configured to independently control each of the actuators 64 as discussed in reference to FIG. 5. Additionally, the controllers 12 may be in communication via a central control system or a distributed control system incorporated in each of the controllers 12. In this configuration, each of the controllers 12 may be configured to identify an orientation of the actuators 64 and the corresponding positions of the lighting modules 46. Based on this information, the system 10 may be configured to map a combined illumination pattern or illumination coverage of each of the emissions that may be emitted from the light sources 20 of the lighting modules 46. As previously discussed, the map of the combined illumination or emission coverage of the combined lighting modules 46 may be programmed into the controllers 12 of the system 10 by one or more calibration methods. In this way, the system 10 may control each lighting module 46 of the head assemblies 50 in concert to provide a scalable, dynamic-lighting system operable to emit the various emissions of light as discussed herein.

As previously discussed, the system 10 may comprise one or more imagers 22. In the exemplary embodiment, the controllers 12*a*, 12*b*, 12*c*, and 12*d* are in communication with a central controller 74. The central controller 74 may comprise or be in communication with one or more of the imagers 22. In such embodiments, the imager 22 of the central controller 74 may be configured to identify one or more obstructions in a region of interest 72. The region of interest 72 may be identified by a location of the marker 26, gesture, input via a user interface, identified by a radio frequency identification tracking device, or programmed into the central controller 74 in relation to a specific procedure. Though discussed in reference to the central controller 74, each of the controllers 12 of the head assemblies 50 may alternatively have a single imager or multiple imagers. In such embodiments, the controllers 12 of each of the head assemblies 50 may be configured to detect the obstructions and communicate among one another to identify the best response to adjust the lighting modules 46 to illuminate the region of interest 72.

The identification of one or more obstructions 76 may be based on a detection of an object in the image data. The obstructions 76 may be identified in response to detecting one or more pulsed infrared emissions emitted from the lighting modules 46. For example, the central controller 74 may be calibrated such that the location of each of a plurality of the detection emitters 20*a* is indicated in programming. Accordingly, by cycling through the detection emitters 20*a* of each of the lighting modules (46*a*, 46*b*, 46*c* . . . 46*m*), the controller may identify a location of the obstructions 76 based on a timed detection of each of the infrared emissions 77. In this way, the central controller 74 may detect a location of the obstructions 76 in relation to a projection trajectory of each of the detection emitters 20*a* to identify a clear or unobstructed trajectory 78. Once the unobstructed trajectory 78 is identified, the central controller 74 may control one or more of the light sources to illuminate the region of interest 72.

In some embodiments, the controllers 12 may communicate within the system 10 to identify the region of interest 72 between two or more of the imagers 22, which may be incorporated in two or more or the lighting modules 46. That is, the two or more of the lighting modules 46 from which the image data is processed to identify the region of interest 72 may be incorporated in a single head assembly 50 or captured by imagers 22 in two or more of the head assemblies 50 (e.g., 50*a* and 50*b*). In this way, the system 10 may operate as a distributed scanning and illumination system formed by the head assemblies 50 and controlled to operate as a unified system via communication among the controllers 12 and/or a central controller.

In general, the central controller 74 or the controllers 12 may be configured to identify one or more light sources 20 of the lighting modules 46 with a line of sight or projection trajectory 78 aligned with the region of interest 72 without interference by one or more obstructions 76. Upon identifying at least one lighting module 46 in one or more of the head assemblies 50 with the clear projection trajectory 78, the central controller 74 may respond by controlling one or more of the controllers 12 to position the at least one lighting module 46 to direct an emission to the region of interest 72. In this configuration, the head assembly array 70 may provide for effective lighting even when tasked with illuminating obstructed regions that change over time.

As an example of a control sequence of the system 10, the system 10 may initially illuminate the table 28 via a lighting module of the second head assembly 50*b* by emitting a second emission 80 of visible light. After the initial operation of the system 10, the imager 22 may detect the obstruction 76 in the field of view 24, which may result in one or more shadows 81 in the region of interest 72. In response to identifying the obstruction 76, the central controller 74 may control controllers 12*a* and 12*b* activating a lighting module of the first head assembly 50*a* that may have the clear projection trajectory 78 via activating a first emission 82 of visible light. Once the first emission 82 is activated, the system 10 may continue to monitor the image data to verify that the first emission 82 remains unobstructed. In this way, the head assembly array 70 may be configured to illuminate the region of interest 72 by controlling a plurality of the head assemblies 50 in combination.

Though specific reference is made to identifying a location of the obstruction 76 and the clear projection trajectory 78 from the image data, the system 10 may utilize one or more algorithms configured to identify and project light to the region of interest 72 via a predictive or experimental algorithm. Such algorithms may apply various inference as well as trial and error to gradually move one or more of the head assemblies 50 and gradually activating the light sources 20 to illuminate the region of interest 72. In these methods as well as others discussed herein, the system may consistently monitor the region or regions of interest 72 for changes or improvements in lighting. In this way, the system 10 may be configured to continue positioning operations that improve the projected trajectory of the light as indicated by the image data from the imagers 22. Such a routine may be applied alone or in combination with the location detection based control discussed herein.

Figure 4:
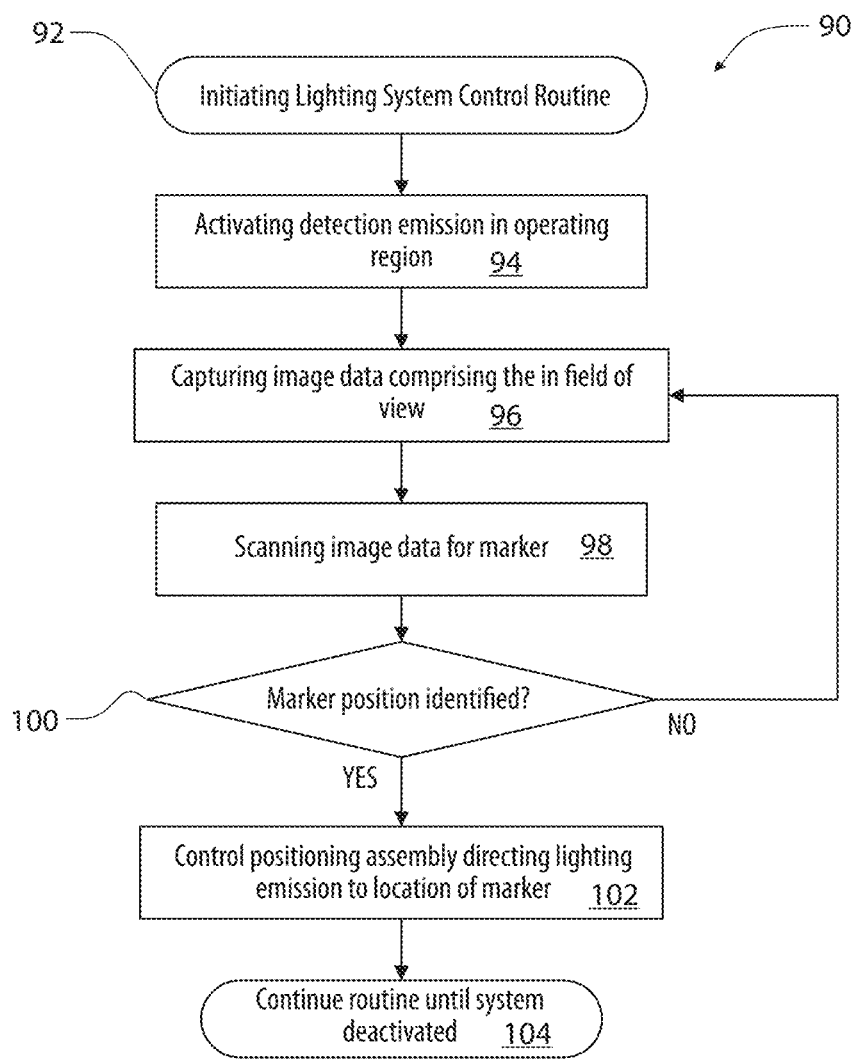
FIG. 4 is a flowchart demonstrating a method for controlling an illumination system.

Referring to FIG. 4, a flowchart for a method 90 for controlling the system 10 is demonstrated. In operation, the method 90 may begin by initializing a control routine of the illumination system 10 (92). Once initiated, the controller 12 may activate the emitter 20*a* to illuminate the operating region 16 in the detection emission 38 (94). In this way, the operating region 16 may be illuminated by the detection emission 38 illuminating various objects that enter the field of view 24 of the imager 22. The controller 12 may then control the imager 22 to capture image data in the field of view 24 (96). Once the image data is captured, the controller 12 may process or scan the image data for various objects including the marker 26 (98).

In step 100, the controller 12 may determine if the position of the marker 26 is identified in the image data. If the position of the marker is not identified, the method 90 may return to steps 96 and 98 to capture and scan the image data in the field of view 24. If the position of the marker 26 is identified in step 100, the controller 12 may control one or more of the positioning or head assemblies 50 to activate the lighting emission(s) 44 directed at the marker 26 (102). Once the position of the marker 26 is identified and illuminated by the lighting emission(s) 44, the controller 12 may continue to track the location of the marker 26 and reposition the head assemblies 50 to maintain a consistent illumination of the marker 26 and the corresponding location (104).

Figure 5:
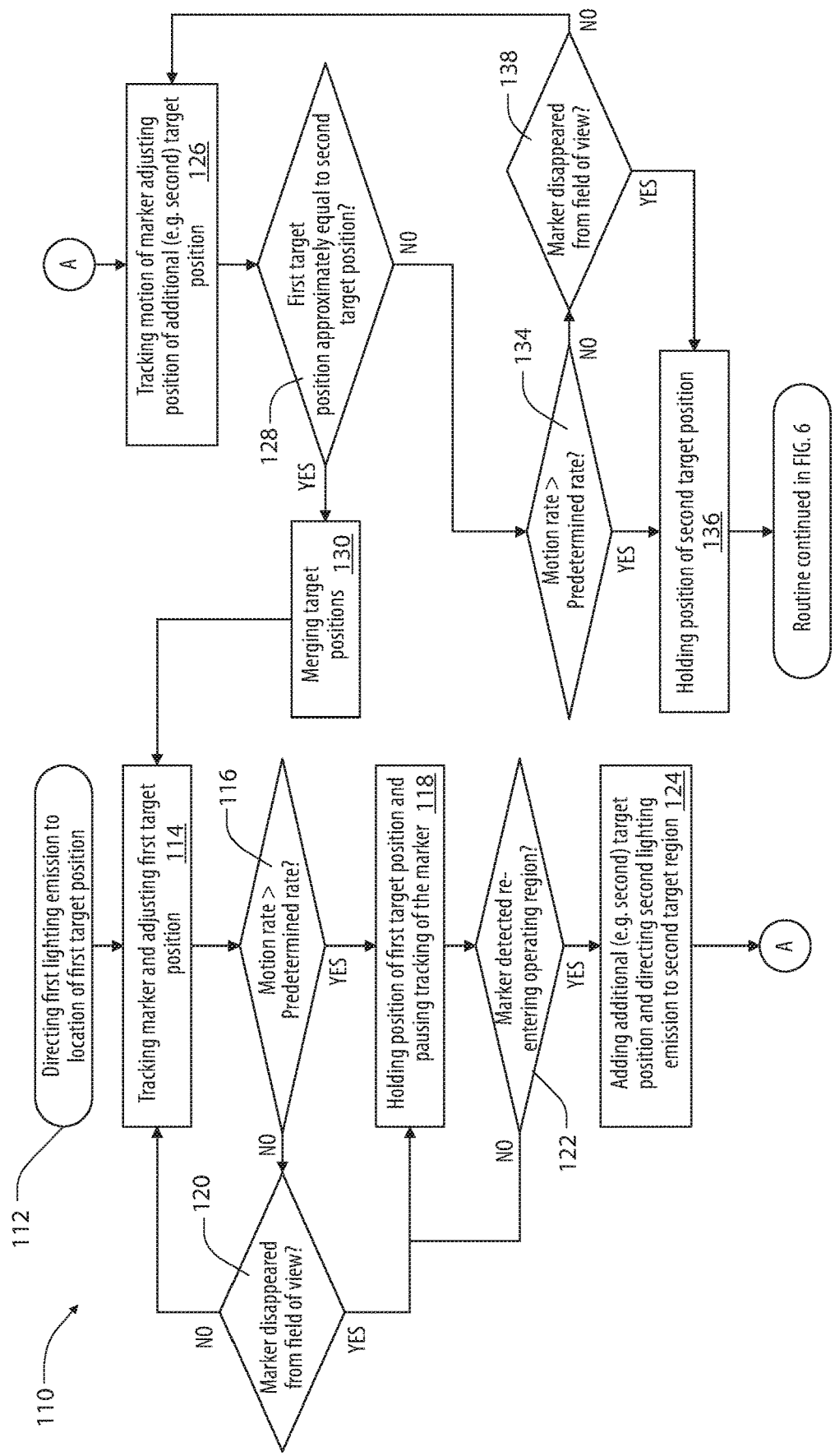
FIG. 5 is a flowchart demonstrating a method for controlling a plurality of illumination regions of an illumination system.
Figure 6:
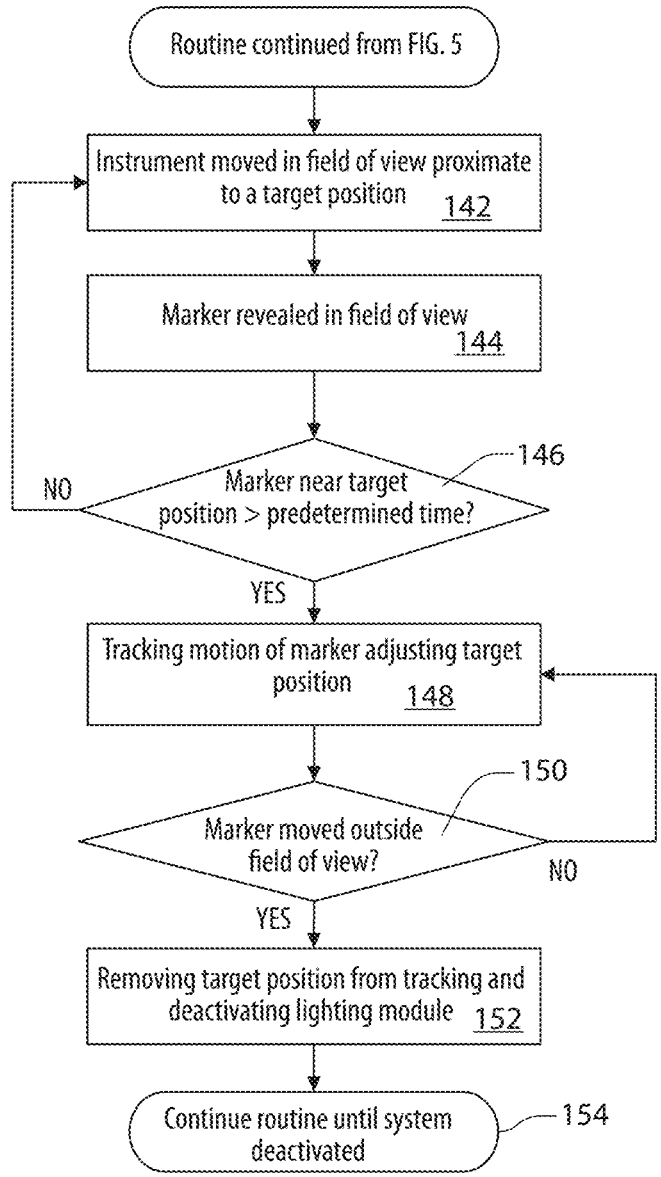
FIG. 6 is a flowchart demonstrating a method for controlling illumination regions of an illumination system continued from FIG. 5.
Figure 7:
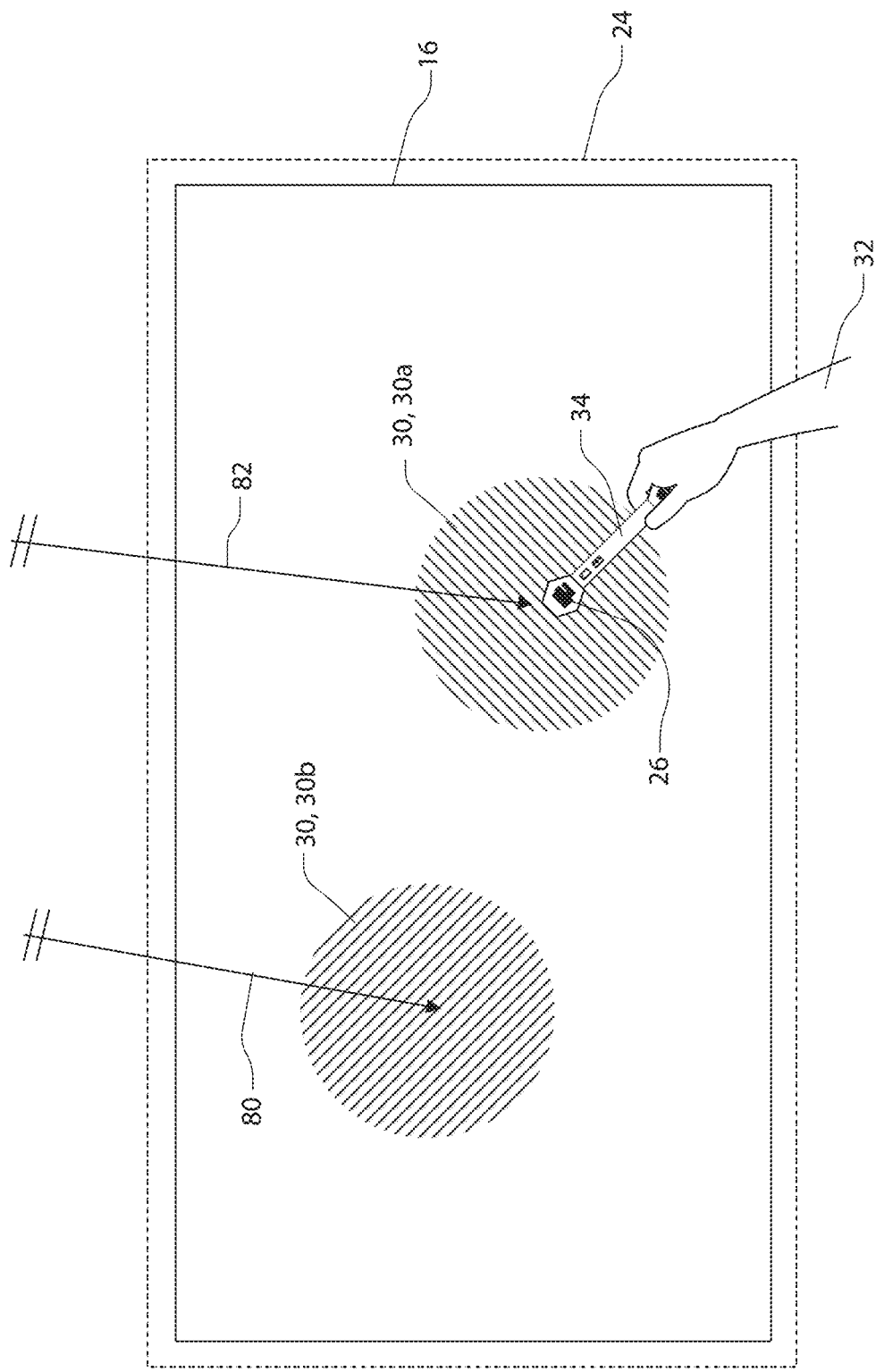
FIG. 7 is an illustrative diagram demonstrating a method for controlling a plurality of illumination regions of an illumination system.

FIGS. 5 and 6 demonstrate a flowchart of a method 110 for controlling the system 10 to adjust the plurality of target regions 30. FIG. 7 demonstrates a simplified diagram of the operating region 16 and the table 28 demonstrating the target regions 30 for discussion in reference to the method 110.

Referring now to FIGS. 3, 5, 6, and 7 as provided by the method 110, the system 10 may be configured to track the motion of the marker 26 on the control instrument 34, which may be manipulated by the user 32 to independently adjust the plurality of target regions 30. Continuing from the method 90, the system 10 may be configured to control a first positioning assembly (e.g. the first head assembly 50a) directing the first emission 82 of visible light to the first target position 30a as discussed in reference to step 102. Additionally, the controller 12 may be configured to identify one or more gestures and/or tracking cues that may be controlled by a user 32 to add a second target position 30b, adjust the positions of each of the target positions, and/or provide for various adjustments to the target regions 30. Throughout the operation of the system 10, the controller 12 may be configured to illuminate each of the target positions by aligning one or more of the lighting emissions 80, 82, etc., from the plurality of positioning assemblies 40 or head assemblies 50 with each of the target regions 30.

Continuing from step 122, in response to the positioning of the first target position 30a, the controller 12 may be configured to track the motion of the marker 26 on the control instrument 34 as previously discussed (114). The motion of the marker 26 may be tracked by the controller 12 in response to the motion being less than a predetermined rate of motion as discussed in reference to step 116. If the rate of motion of the marker 26 exceeds the predetermined rate, the controller 12 may hold or set the location of the first target position 30a (118). Additionally, if the marker 26 is removed or otherwise disappears from the field of view 24 in step 120, the controller 12 may set the first target position 30a (118). Adjustment of the target regions 30 is further discussed in reference to FIG. 6.

Following step 118, or following the pausing of the tracking in various steps discussed herein, the controller 12 may further be configured to detect the marker 26 exiting, entering, and/or re-entering the operating region 16 of the field of view 24 (122). In response to the marker 26 entering the operating region 16 of the field of view 24, the controller 12 may identify the location of the marker 26 and add an additional target, which is discussed in reference to the second target position 30b (124). Once the second target position 30b is added, the controller 12 may control the head assemblies 50 to align the first emission 82 with the first target position 30a and the second emission 80 with the second target position 30b. In response to adding the second target position 30b, the controller 12 may track changes in the position of the marker 26 and adjust the second target position 30b to align with the location of the marker 26 (126). In this way, the second target position 30b may be added and illuminated by one or more of the lighting modules 46.

Following step 126, the controller 12 may continue to track the position of the marker 26 in the field of view 24 and update the second target position 30b. The controller 12 may further identify if the first target position 30a is approximately equal to the second target position 30b in step 128. The approximate equality of the target regions 30a and 30b may be identified in response to the controller 12 identifying that the target regions 30a and 30b are positioned by the marker 26 within a predetermined range (e.g. a 10 cm diameter region) for a predetermined period of time (e.g. 3 seconds). In response to identifying that the target regions 30a and 30b are positioned by the marker 26 within a predetermined range for the predetermined time, the controller 12 may selectively merge the first target position 30a and the second target position 30b and return to step 114.

If the target regions 30 are not merged, the controller 12 may continue to track the position of the marker 26 in the field of view 24 and adjust the second target position 30b. The motion of the marker 26 may be tracked by the controller 12 in response to the motion being less than a predetermined rate of motion (134). If the rate of motion of the marker 26 exceeds the predetermined rate, the controller 12 may hold or set the location of the second target position 30b (136). Additionally, if the marker 26 is removed or otherwise disappears from the field of view 24 in step 138, the controller 12 may set or hold the second target position 30b to the last identified location of the marker 26 (136). As previously discussed, the method 110 may further continue in reference to FIG. 6, which may provide for the adjustment of the target regions 30.

Referring now to FIGS. 6 and 7, a lighting position adjustment routine is discussed, which may begin following either of steps 118 and/or 136 from FIG. 5. As discussed in FIG. 6, the routine may be in reference to either of the target regions 30a, 30b or additional target regions 30. In order to reposition either of the target regions 30, the user 32 may move the control instrument 34 into the field of view 24 such that the marker 26 is proximate to the location of either of the first target position 30a or the second target position 30b (142). When positioning the maker 26, the user 32 may arrange the control instrument 34 such that the marker 26 is hidden, or concealed from the field of view 24. In such examples, the maker 26 may only be displayed on one side of the instrument 34. The proximity to each of the positions 30 for repositioning as discussed herein may be within approximately 5 cm to 20 cm depending on a desired accuracy or sensitivity of the system 10. The location of the instrument 34 and the marker 26 relative to each of the target regions 30 may be visibly apparent to the user 32 because the positions 30 may be illuminated by the emissions 80, 82, etc.

Once the instrument 34 is located proximate to one of the target regions 30a, 30b, etc., the user 32 may reveal the marker 26 in the field of view 24 (144). In step 146, the controller 12 may then identify if the marker 26 is proximate to one of the target regions 30 for greater than a predetermined time (e.g. 3-5 sec.). In response to identifying the marker 26 proximate to either of the target regions 30 for the predetermined period of time (e.g. 3 seconds), the controller 12 may adjust the location of the target position 30a or 30b in the operating region 16 based on the location of the marker 26 in the field of view 24 as previously discussed in reference to steps 114 and 126 (148).

In step 150, the controller 12 may continue to adjust the target position (e.g. 30a, 30b, etc.) based on the location of the marker 26. If the marker 26 is moved outside the operating region 16, the controller 12 may remove the corresponding target position (e.g. 30a, 30b, etc.) and deactivate or reassign the lighting emission (e.g. 80, 82) and the corresponding lighting module(s) 46 from illuminating the target position (e.g. 30a, 30b, etc.) (152). Following the removal of one of the target regions 30, the controller 12 may continue to the method 110 until the system is deactivated (154).

Figure 8:
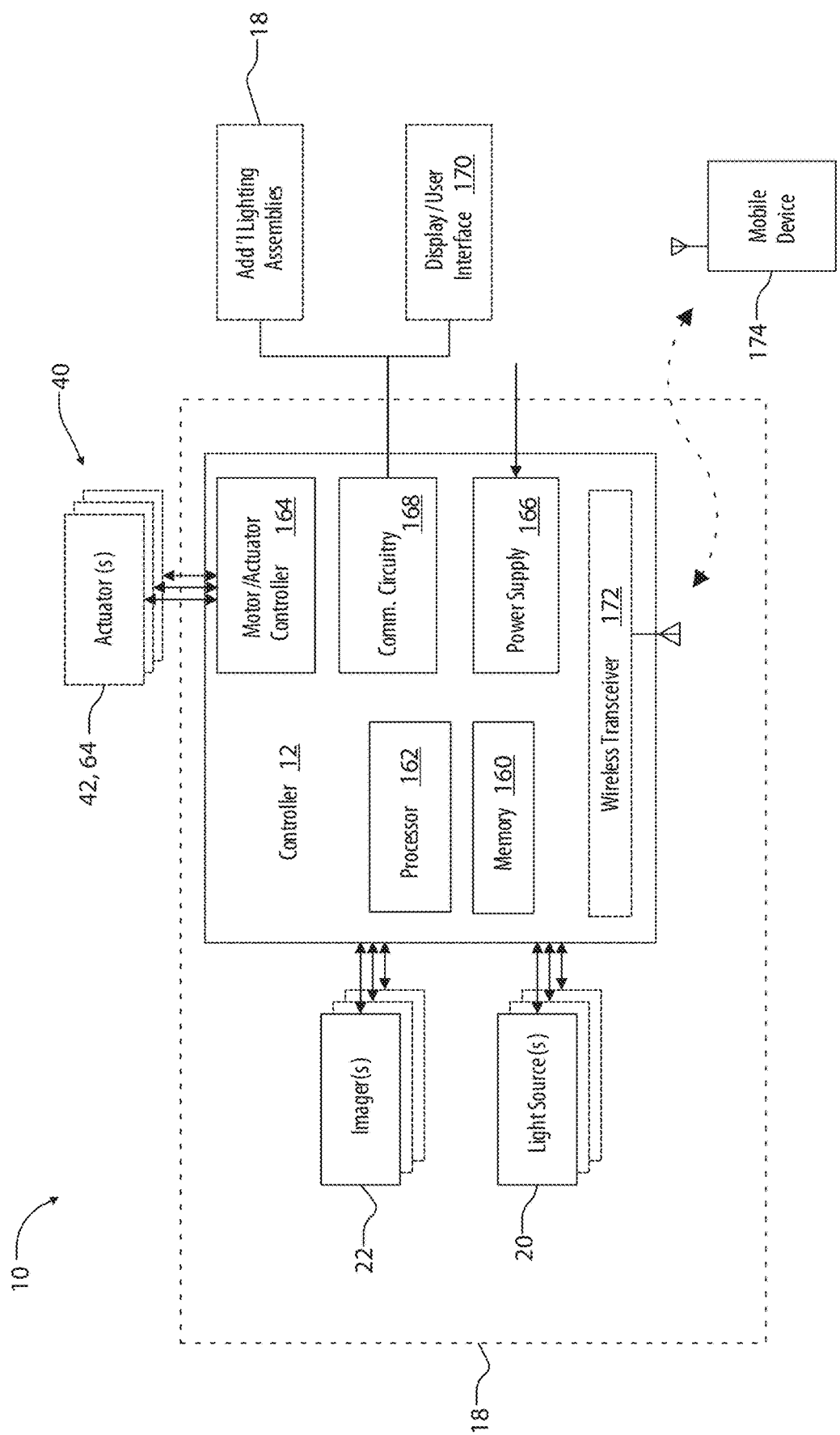
FIG. 8 is a block diagram demonstrating the illumination system in accordance with the disclosure.

Referring to FIG. 8, a block diagram of an illumination system 10 is shown. As discussed herein, the illumination system 10 may include one or more imagers 22 configured to capture image data from the medical suite 14 and/or from the operating region 16 as shown in FIGS. 1 and 3. The imagers 22 may be configured to relay visual information to the controller 12 of the illumination system 10. The controller 12 may include a memory 160 and a processor 162.

The memory 160 may store computer-executable commands (e.g., routines) which are controlled by the processor 162. According to various examples, the memory 160 may include a light control routine and/or an image analyzing routine. In exemplary embodiments, the memory 160 may include the lighting control method 90.

Once the image analyzing routine has processed the image data from the imager 22, the controller 12 may communicate one or more control instructions to a motor or actuator controller 164. In response to the control signals, the motor controller 164 may control the actuators 42, 64 or the positioning assemblies 40 to move, steer, or otherwise adjust an orientation of the light assemblies 18. In this way, the controller 12 may direct the lighting assemblies 18 to emit the lighting emission 44 and/or direct the field of view 24 to a desired location, which may correspond to the location of the marker 26. The system 10 may additionally comprise one or more power supplies 166. The power supplies 166 may provide for one or more power supplies or ballasts for various components of the lighting assembly 18 as well as the actuators 42, 64 or positioning assemblies 40.

In some embodiments, the system 10 may further comprise one or more communication circuits 168, which may be in communication with the processor 162. The communication circuit 168 may be configured to communicate data and control information to a display or user interface 170 for operating the system 10. The interface 170 may comprise one or more input or operational elements configured to control the system 10 and communicate data. The communication circuit 168 may further be in communication with additional lighting assemblies 18, which may operate in combination as an array of lighting assemblies. The communication circuit 168 may be configured to communicate via various communication protocols. For example, communication protocols may correspond to process automation protocols, industrial system protocols, vehicle protocol buses, consumer communication protocols, etc. Additional protocols may include, MODBUS, PROFIBUS, CAN bus, DATA HIGHWAY, DeviceNet, Digital multiplexing (DMX512), or various forms of communication standards.

In various embodiments, the system 10 may comprise a variety of additional circuits, peripheral devices, and/or accessories, which may be incorporated into the system 10 to provide various functions. For example, in some embodiments, the system 10 may comprise a wireless transceiver 172 configured to communicate with a mobile device 174. In such embodiments, the wireless transceiver 172 may operate similar to the communication circuit 168 and communicate data and control information for operating the system 10 to a display or user interface of the mobile device 174. The wireless transceiver 172 may communicate with the mobile device 174 via one or more wireless protocols (e.g. Bluetooth®; Wi-Fi (802.11a, b, g, n, etc.); ZigBee®; and Z-Wave®; etc.). In such embodiments, the mobile device 174 may correspond to a smartphone, tablet, personal data assistant (PDA), laptop, etc.

In various embodiments, the light sources 20 may be configured to produce unpolarized and/or polarized light of one handedness including, but not limited to, certain liquid crystal displays (LCDs), laser diodes, light-emitting diodes (LEDs), incandescent light sources, gas discharge lamps (e.g., xenon, neon, mercury), halogen light sources, and/or organic light-emitting diodes (OLEDs). In polarized light examples of the light sources 20, the light sources 20 are configured to emit a first handedness polarization of light. According to various examples, the first handedness polarization of light may have a circular polarization and/or an elliptical polarization. In electrodynamics, circular polarization of light is a polarization state in which, at each point, the electric field of the light wave has a constant magnitude, but its direction rotates with time at a steady rate in a plane perpendicular to the direction of the wave.

As discussed, the light assemblies 18 may include one or more of the light sources 20. In examples including a plurality of light sources 20, the light sources 20 may be arranged in an array. For example, an array of the light sources 20 may include an array of from about 1×2 to about 100×100 and all variations therebetween. As such, the light assemblies 18 including an array of the light sources 20 may be known as pixelated light assemblies 18. The light sources 20 of any of the light assemblies 18 may be fixed or individually articulated. The light sources 20 may all be articulated, a portion may be articulated, or none may be articulated. The light sources 20 may be articulated electro-mechanically (e.g., a motor) and/or manually (e.g., by a user). In static, or fixed, examples of the light sources 20, the light sources 20 may be assigned to focus on various predefined points (e.g., on a patient and/or on the table 28).

Modifications of the disclosure will occur to those skilled in the art and to those who make or use the disclosure. Therefore, it is understood that the embodiments shown in the drawings and described above are merely for illustrative purposes and not intended to limit the scope of the disclosure, which is defined by the following claims as interpreted according to the principles of patent law, including the Doctrine of Equivalents.

It will be understood by one having ordinary skill in the art that construction of the described disclosure, and other components, is not limited to any specific material. Other exemplary embodiments of the disclosure disclosed herein may be formed from a wide variety of materials unless described otherwise herein.

For purposes of this disclosure, the term "coupled" (in all of its forms: couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, are illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system 10 may be varied, and the nature or numeral of adjustment positions provided between the elements may be varied. It should be noted that the elements and/or assemblies of the system 10 may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes, or steps within described processes, may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further, it is to be understood that such concepts are intended to be covered by the following claims, unless these claims, by their language, expressly state otherwise. Further, the claims, as set forth below, are incorporated into and constitute part of this Detailed Description.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about," and one not modified by "about." It will be further understood that the end-points of each of the ranges are significant both in relation to the other end-point and independently of the other end-point.

The terms "substantial," "substantially," and variations thereof as used herein are intended to note that a described feature is equal or approximately equal to a value or description. For example, a "substantially planar" surface is intended to denote a surface that is planar or approximately planar. Moreover, "substantially" is intended to denote that two values are equal or approximately equal. In some embodiments, "substantially" may denote values within about 10% of each other, such as within about 5% of each other, or within about 2% of each other.

What is claimed is:

1. An illumination system for a room, comprising:
a light assembly comprising at least one illumination source configured to selectively direct a first light emission and a second light emission in an operating region of the room;
an imager configured to capture image data in a field of view in the room;
a controller in communication with the light assembly and the imager, wherein the controller is configured to:
detect a position of a marker in the image data;
control the light assembly to direct the first light emission to a first target position within the operating region based on the position of the marker;
in response to detecting the marker in the operating region, control the light assembly to direct a second light emission to a second target position within the region based on a second position of the marker;
in response to identifying a change in the position of the marker at a rate of motion within a predetermined velocity range in the field of view, track the motion of the marker within the operating region; and
set a target location for the at least one lighting region in response to the rate of motion exceeding the predetermined velocity range.

2. The system according to claim 1, wherein the controller is further configured to:
detect the marker in the image data entering the operating region of the field of view from outside an operating perimeter of the operating region.

3. The system according to claim 2, wherein the operating perimeter is located within the field of view and defines a work surface.

4. The system according to claim 1, wherein the controller is further configured to:
independently adjust the first target position and the second target position in response to the position of the marker.

5. The system according to claim 4, wherein the controller is further configured to:
control the light assembly to merge a first lighting region illuminated by the first light emission with a second lighting region illuminated by the second light emission such that the first lighting region overlaps the second lighting region over a portion of the operating region.

6. The system according to claim 4, wherein the controller is further configured to:
in response to a first lighting region of the first light emission overlapping a second lighting region of the second light emission for a predetermined period of time, merge the first lighting region of the first light emission with the second lighting region of the second light emission.

7. The system according to claim 3, wherein the controller is further configured to:
selectively control the first target location of a first lighting region of the first light emission in response to identifying the marker proximate to the first lighting region for a predetermined period of time.

8. The system according to claim 7, wherein the controller is further configured to:
selectively control the second target location of a second lighting region of the second light emission in response to identifying the marker proximate to the second lighting region for the predetermined period of time.

9. The system according to claim 1, wherein the controller is further configured to:
control the first target location of the first lighting region to change commensurate to the motion of the marker within the operating region.

10. A method for controlling a light assembly comprising at least one illumination source configured to selectively direct a plurality of light emissions in an operating region of a room, the method comprising:
capturing image data in a field of view in the room;
detecting a position of a marker in the image data;
directing a first light emission to a first target position within the operating region based on the position of the marker;
maintaining the first light emission in the first target position;
detecting the marker in the image data entering the operating region of the field of view from outside an operating perimeter of the operating region;

in response to detecting the marker entering the operating region, controlling the light assembly to direct a second light emission to a second target position within the operating region based on the position of the marker, wherein the second target position is independently tracked from the first target position during an overlapping temporal period; and set the first target location for the first lighting region in response to the marker disappearing from the image data in the operating region.

11. The method according to claim 10, further comprising:

controlling the first target location of a first lighting region of the first light emission in response to identifying the marker proximate to the first lighting region for a first predetermined period of time.

12. The method according to claim 11, further comprising:

controlling the second target location of a second lighting region of the second light emission in response to identifying the marker proximate to the second lighting region for a second predetermined period of time.

13. The method according to claim 11, further comprising:

in response to identifying a change in the position of the marker at a rate of motion within a predetermined velocity range in the field of view, tracking the motion of the marker within the operating region.

14. The method according to claim 13, further comprising:

controlling the first target location of the first lighting region to change commensurate to the motion of the marker within the operating region.

15. The method according to claim 10, further comprising:

in response to a first lighting region of the first light emission overlapping a second lighting region of the second light emission fora predetermined period of time, merging the first lighting region of the first light emission with the second lighting region of the second light emission.

16. An illumination system for a room, comprising:

a light assembly comprising at least one illumination source configured to selectively direct at least one light emission in an operating region of the room;

an imager configured to capture image data in a field of view in the room;

a controller in communication with the light assembly and the imager, wherein the controller is configured to:

control the light assembly to direct a first emission illuminating a first region and a second emission illuminating a second region of the operating region, wherein the first region and the second region are spatially separated in the operating region;

detect a position of a marker in the image data;

selectively control a first target location of the first emission in response to identifying the marker proximate to the first region for a first predetermined period of time;

selectively control a second target location of the second emission in response to identifying the marker proximate to the second region for a second predetermined period of time, wherein the second target location is controlled independently of the first target position;

detect the first target location overlapping the second target location; and in response to the overlapping for a third predetermined period of time, merge the first region of the first light emission with the second region of the second light emission by combining the first target position and the second target position.

* * * * *

UNITED STATES PATENT AND TRADEMARK OFFICE
CERTIFICATE OF CORRECTION

PATENT NO. : 11,039,900 B2
APPLICATION NO. : 16/732577
DATED : June 22, 2021
INVENTOR(S) : Hallack et al.

Page 1 of 1

It is certified that error appears in the above-identified patent and that said Letters Patent is hereby corrected as shown below:

In the Claims

Column 17, Line 38, "fora" should be --for a--.

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*